(12) United States Patent
Uragg et al.

(10) Patent No.: US 7,569,585 B2
(45) Date of Patent: Aug. 4, 2009

(54) 1, 5-DIAMINOPENTAN-3-OL COMPOUNDS AND RELATED TREATMENT METHODS

(75) Inventors: Heinz Uragg, Stolberg (DE); Corinna Maul, Aachen (DE); Helmut Buschmann, Esplugues de Llobregat (ES); Bernd Sundermann, Aachen (DE); Werner Englberger, Stolberg (DE)

(73) Assignee: Gruenenthal GmbH, Aachen (DE)

( * ) Notice: Subject to any disclaimer, the term of this patent is extended or adjusted under 35 U.S.C. 154(b) by 633 days.

(21) Appl. No.: 10/866,088

(22) Filed: Jun. 14, 2004

(65) Prior Publication Data

US 2005/0020562 A1   Jan. 27, 2005

Related U.S. Application Data

(63) Continuation of application No. PCT/EP02/13912, filed on Dec. 9, 2002.

(30) Foreign Application Priority Data

Dec. 14, 2001   (DE)   ............................. 101 61 818

(51) Int. Cl.
  *A61K 31/445*   (2006.01)
  *C07D 401/06*   (2006.01)
(52) U.S. Cl. .......................... 514/316; 546/187
(58) Field of Classification Search .............. 546/187; 514/316
  See application file for complete search history.

(56) References Cited

U.S. PATENT DOCUMENTS

| 2,948,722 | A | * | 8/1960 | Biel .......................... 544/128 |
| 4,366,172 | A |   | 12/1982 | Lednicer |
| 4,442,103 | A | * | 4/1984 | Saari ..................... 514/253.01 |
| 4,923,865 | A | * | 5/1990 | Cossement et al. ....... 514/235.8 |
| 5,801,201 | A |   | 9/1998 | Graudums et al. |
| 6,410,790 | B1 |  | 6/2002 | Sundermann et al. |

2003/0008859 A1   1/2003   Sundermann et al.

FOREIGN PATENT DOCUMENTS

| AT | E 28 628 | 4/1979 |
| DE | 28 39 891 | 4/1979 |
| DE | 195 47 766 A1 | 6/1997 |
| DE | 692 21 919 T2 | 10/1997 |
| DE | 199 15 601 A1 | 10/2000 |
| DE | 199 63 175 A1 | 7/2001 |
| EP | 0 112 669 | 7/1987 |
| EP | 0 506 478 B1 | 9/1997 |
| GB | 783 627 | 9/1957 |

OTHER PUBLICATIONS

Equi et al. "Oxidation of putrescine and . . . " CA 114:164573 (1991).*
King et al. "alpha sub 2 adrenergic . . . " PASCAL No. 82-0146497 (1982).*
Shouse et al. "The alpha sub 2 adrenoreceptor . . . " PASCAL No. 96-0425050 (1996).*
Spencer et al. :Ephedrine inhbits . . . BIOSIS No. 200510318615.*
Barrett "Substituted pyrrocolines" CA52:40773 (1955).*
Blick et al. "Disubstitution of cycloalkanones . . . " CA 54:28385 (1959).*
Radbruch et al. "A risk benefit . . . " CA 125:157519 (1996).*
Obata et al. "Evaluation and structure-activity . . . " CA 134:335974 (2001).*
Rojas et al. "Role of 5-HT1A . . . " CA 142:367488 (2005).*
Barrett et al. "Aminoalkyl tertiary . . . " CA 52:65844 (1958).*
Biel et al. "1-(1,2,3,4-tetrahydroisoquinolino . . . " CA 55:13517 (1961).*
Pascal et al. "New antihistaminic theophylline . . . " CA 102:166527 (1985).*
Salminen et al. "Three dimensional model . . . " J. Biol. chem. v.274, p. 23405-23413 (1999).*
Blicke et al., *Disubstitution of Cycloalkanones in the Mannich Reaction*, J. Org. Chem., vol. 24, 1959, pp. 1069-1076.
International Search Report.

* cited by examiner

*Primary Examiner*—Celia Chang
(74) *Attorney, Agent, or Firm*—Crowell & Moring LLP

(57) ABSTRACT

Substituted 1,5-diaminopentan-3-ol compounds and methods of making the same. Pharmaceutical compositions containing these compounds and methods of treatment using these pharmaceutical compositions.

17 Claims, No Drawings

1,5-DIAMINOPENTAN-3-OL COMPOUNDS AND RELATED TREATMENT METHODS

CROSS REFERENCE TO RELATED APPLICATIONS

This application is a continuation of International Patent Application No. PCT/EP02/13912, filed Jun. 26, 2003, designating the United States of America, and published in German as WO 03/051819, the entire disclosure of which is incorporated herein by reference. Priority is claimed based on Federal Republic of Germany Patent Application No. 101 61 818.2, filed Dec. 14, 2001.

FIELD OF THE INVENTION

The present invention relates to substituted 1,5-diaminopentan-3-ol compounds, to methods for their production, to pharmaceutical compositions containing these compounds and to the use of substituted 1,5-diaminopentan-3-ol compounds for producing pharmaceutical compositions and in related treatment methods.

BACKGROUND OF THE INVENTION

The treatment of pain has great importance in medicine. There is a worldwide need for effective methods of treating pain. The urgent need for action for patient-friendly and purposeful treatment of chronic and non-chronic pain conditions, this being taken to mean the successful and satisfactory treatment of pain for the patient, is documented in the large number of scientific papers which have recently appeared in the field of applied analgesics and fundamental research on nociception.

Conventional opioids, such as morphine, are extremely effective in the treatment of severe to the severest pain. However, their undesirable side effects include inter alia respiratory depression, nausea, sedation, constipation and tolerance development. In addition, they are less effective in the event of neuropathic or incidental pain, suffered in particular by patients with tumors.

SUMMARY OF THE INVENTION

One object of the present invention is to provide new compounds which may be used as active pharmaceutical ingredients in pharmaceutical compositions and which are particularly suitable for controlling pain, in particular chronic and/or non-chronic pain.

This object is achieved according to the invention by providing substituted 1,5-diaminopentan-3-ol compounds corresponding to formula I, as these compounds have a particularly pronounced analgesic effect and may be used to treat pain, in particular chronic and/or non-chronic pain, as a local anaesthetic, an anti-arrhythmic, anti-emetic and/or nootropic (neurotropic), for the treatment of inflammatory and/or allergic reactions, cardiovascular diseases, urinary incontinence, diarrhea, gastritis, ulcers, shock, migraine, narcolepsy, obesity, asthma, glaucoma, tinnitus, hyperkinetic syndrome, pruritus, alcohol and/or drug and/or medicine abuse and/or dependency and/or inflammation and/or depression and/or to increase alertness, to increase libido and/or for the treatment of neurodegenerative diseases, in particular Parkinson's disease and Huntington's chorea, for the treatment and/or prophylaxis of epilepsy, schizophrenia, Alzheimer's disease, stroke, cerebral ischemia, cerebral infarct, cerebral oedema and/or for anxiolysis and/or anaesthesia.

The present invention therefore relates to 1,5-diaminopentan-3-ol compounds corresponding to formula I

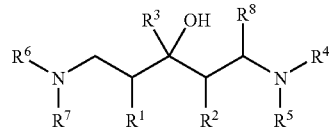

wherein $R^1$ and $R^2$ are the same or different and each represent a linear or branched, saturated or unsaturated aliphatic radical or together form a $(CH_2)_n$ chain, wherein n represents an integer greater than or equal to 3, $R^3$ represents a linear or branched, saturated or unsaturated aliphatic radical, a saturated or unsaturated cycloaliphatic radical, an aryl radical or a heteroaryl radical, wherein the respective ring system may optionally be singly or multiply substituted and/or be bound by a linear or branched, saturated or unsaturated aliphatic bridge and/or the aryl or heteroaryl radical may be part of a polycyclic system.

$R^4$ and $R^5$ are the same or different and each represent a linear or branched, saturated or unsaturated aliphatic radical or an aryl radical bound by a linear or branched, saturated or unsaturated aliphatic bridge or together form a $(CH_2)_m$ chain wherein m represents an integer, $R^6$ and $R^7$ are the same or different and each represent a linear or branched, saturated or unsaturated aliphatic radical or an aryl radical bound by a linear or branched, saturated or unsaturated aliphatic bridge or together form a $(CH_2)_p$ chain, wherein p represents an integer, $R^8$ represents hydrogen or an optionally singly or multiply substituted aryl or heteroaryl radical, wherein the aryl or heteroaryl radical may be part of a polycyclic system, in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates, with the exception of the compounds 1,5-bis-(N,N'-dimethylamino)-2,4-dimethyl-3-pyridin-2-ylpentan-3-ol, 2,6-bis-[(N,N'-dimethylamino)methyl]-1-phenylcyclohexanol, 2,6-bis-[(N,N'-dimethylamino)methyl]-1-pyridin-2-ylcyclohexanol and 2,7-bis-[(N,N'-dimethylamino)methyl]-1-pyridin-2-ylcycloheptanol.

Preferred compounds are those corresponding to formula I, wherein $R^1$ and $R^2$ are the same or different and each represent a linear or branched, saturated or unsaturated aliphatic $C_{1-6}$ radical or together form a $(CH_2)_n$ chain, wherein n represents an integer from 3 to 9, $R^3$ represents a linear or branched, saturated or unsaturated aliphatic $C_{1-6}$ radical, a saturated or unsaturated cycloaliphatic $C_{3-7}$ radical, a phenyl radical or a five- or six-membered heteroaryl radical, wherein the respective ring system may optionally be singly or multiply substituted and/or be bound by a linear or branched, saturated or unsaturated aliphatic $C_{1-5}$ bridge, $R^4$ and $R^5$ are the same or different and each represent a linear or branched, saturated or unsaturated aliphatic $C_{1-6}$ radical, a phenyl radical bound by a linear or branched, saturated or unsaturated aliphatic $C_{1-5}$ bridge or together form a $(CH_2)_m$ chain, wherein m represents an integer from 4 to 10, $R^6$ and $R^7$ are the same or different and each represent a linear or branched, saturated or unsaturated aliphatic $C_{1-6}$ radical, a phenyl radical bound by a linear or branched, saturated or unsaturated aliphatic $C_{1-5}$ bridge or together form a $(CH_2)_p$ chain, wherein p represents an integer from 4 to 10, $R^8$ represents hydrogen in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates, with the exception of the compounds 1,5-bis-(N,N'-dimethylamino)-2,4-dimethyl-3-pyridin-2-ylpentan-3-ol, 2,6-bis-[(N,N'-dimethylamino)methyl]-1-phenylcyclohexanol, 2,6-bis-[(N,N'-dimethylamino)methyl]-1-pyridin-2-ylcyclohexanol and 2,7-bis-[(N,N'-dimethylamino)methyl]-1-pyridin-2-ylcycloheptanol.

Other preferred compounds include those corresponding to formula I, wherein $R^1$ and $R^2$ are the same or different and each represent a linear or branched, saturated or unsaturated aliphatic $C_{1-3}$ radical or together form a $(CH_2)_n$ chain, wherein n represents an integer from 3 to 5, $R^3$ represents a linear or branched, saturated or unsaturated aliphatic $C_{1-3}$ radical, a saturated or unsaturated cycloaliphatic $C_{5-6}$ radical, a phenyl radical or a five- or six-membered heteroaryl radical, wherein the respective ring system may optionally be singly or multiply substituted by halogen, an alkyl group, an alkoxy group and/or a trihalogenated alkyl group and/or be bound by a linear or branched, saturated or unsaturated aliphatic $C_{1-3}$ bridge, $R^4$ and $R^5$ are the same or different and each represent a linear or branched, saturated or unsaturated aliphatic $C_{1-3}$ radical or together form a $(CH_2)_m$ chain, wherein m represents an integer from 4 to 6, $R^6$ and $R^7$ are the same or different and each represent a linear or branched, saturated or unsaturated aliphatic $C_{1-3}$ radical or together form a $(CH_2)_p$ chain, wherein p represents an integer from 4 to 6, $R^8$ represents hydrogen in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates, with the exception of the compounds 1,5-bis-(N,N'-dimethylamino)-2,4-dimethyl-3-pyridin-2-ylpentan-3-ol, 2,6-bis-[(N,N'-dimethylamino)methyl]-1-phenylcyclohexanol, 2,6-bis-[(N,N'-dimethylamino)methyl]-1-pyridin-2-ylcyclohexanol and 2,7-bis-[(N,N'-dimethylamino)methyl]-1-pyridin-2-ylcycloheptanol.

Other preferred compounds include those corresponding to formula I, wherein $R^1$ and $R^2$ together form a $(CH_2)_n$ chain, wherein n represents 3, $R^3$ represents a vinyl radical, a cyclopentyl radical, a cyclohexyl radical, a thiophenyl radical or a phenyl radical, wherein the cyclohexyl radical may optionally be bound by a methylene bridge or the phenyl radical may optionally be singly or multiply substituted by fluorine, chlorine, a methyl group, an isopropyl group, a methoxy group and/or a trifluoromethyl group and/or may optionally be bound by a linear, saturated aliphatic $C_{1-3}$ bridge or an ethinyl bridge, $R^4$ and $R^5$ together form a $(CH_2)_m$ chain, wherein m represents 5, $R^6$ and $R^7$ together form a $(CH_2)_p$ chain, wherein p represents 5, $R^8$ represents hydrogen in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates.

Particularly preferred compounds include those corresponding to formula II

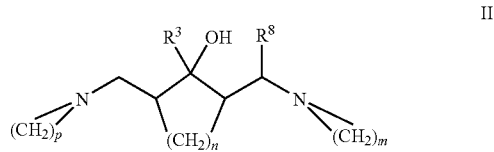

II wherein m and p are the same or different and represent an integer from 4 to 10, n represents an integer greater than or equal to 3

$R^3$ represents a linear or branched, saturated or unsaturated aliphatic radical, a saturated or unsaturated cycloaliphatic radical, an aryl radical or a heteroaryl radical, wherein the respective ring system may optionally be singly or multiply substituted and/or be bound by a linear or branched, saturated or unsaturated aliphatic bridge and/or the aryl or heteroaryl radical may be part of a polycyclic system and $R^8$ represents hydrogen or an optionally singly or multiply substituted aryl or heteroaryl radical, wherein the aryl or heteroaryl radical may be part of a polycyclic system, in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates.

Other preferred compounds include those corresponding to formula II, wherein m and p are the same or different and represent an integer from 4 to 10, n represents an integer from 3 to 9 and $R^3$ represents a linear or branched, saturated or unsaturated aliphatic $C_{1-6}$ radical, a saturated or unsaturated cycloaliphatic $C_{3-7}$ radical, a phenyl radical or a five- or six-membered heteroaryl radical, wherein the respective ring system may optionally be singly or multiply substituted and/or bound by a linear or branched, saturated or unsaturated aliphatic $C_{1-5}$ bridge, $R^8$ represents hydrogen in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates.

Other preferred compounds include those corresponding to II, wherein m and p are the same or different and represent an integer from 4 to 6, n represents an integer from 3 to 5 and $R^3$ represents a linear or branched, saturated or unsaturated aliphatic $C_{1-3}$ radical, a saturated or unsaturated cycloaliphatic $C_{5-6}$ radical, a phenyl radical or a five- or six-membered heteroaryl radical, wherein the respective ring system may optionally be singly or multiply substituted by halogen, an alkyl group, an alkoxy group and/or a trihalogenated alkyl group and/or be bound by a linear or branched, saturated or unsaturated aliphatic $C_{1-3}$ bridge, $R^8$ represents hydrogen in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates.

Other preferred compounds include those corresponding to formula II, wherein m and p represent 5, n represents 3 and $R^3$ represents a vinyl radical, a cyclopentyl radical, a cyclohexyl radical, a thiophenyl radical or a phenyl radical, wherein the cyclohexyl radical may optionally be bound by a methylene bridge or the phenyl radical may optionally be singly or multiply substituted by fluorine, chlorine, a methyl group, an isopropyl group, a methoxy group and/or a trifluoromethyl group and/or may optionally be bound by a linear, saturated aliphatic $C_{1-3}$ bridge or an ethinyl bridge, and $R^8$ represents hydrogen in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salts, or in the form of their solvates, in particular the hydrates.

A heteroaryl radical is taken to mean an optionally singly or multiply substituted, five- or six-membered aromatic radical with at least 1, possibly also 2, 3, 4 or 5 heteroatoms, which may be the same or different, which may be part of a polycylic system. Preferred heteroatoms are nitrogen, oxygen and sulphur. It is particularly preferred if the heteroaryl radicals are selected from the group comprising pyrrolyl, indolyl, furyl (furanyl), benzofuranyl, thienyl (thiophenyl), benzothienyl, pyrazolyl, imidazolyl, thiazolyl, oxazolyl, isoxazoyl, pyridinyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl radical. The bond may be made by any arbitrary ring atom capable of being bound. The optionally present substituents may be the same or different and be bound to any arbitrary ring atom capable of being bound.

An aryl radical is taken to mean an optionally singly or multiply substituted aromatic radical which may be part of a polycyclic system. A phenyl radical is particularly preferred. The bond can be made by any arbitrary ring atom capable of being bound. The substituents optionally present may be the same of different and be bound to any arbitrary ring atom capable of being bound.

Particularly preferred compounds include those selected from the group comprising 1-phenyl-2,6-bis-piperidin-1-ylmethyl-cyclohexanol, 1-(4-chlorophenyl)-2,6-bis-piperidin-1-ylmethyl-cyclohexanol, 1-benzyl-2,6-bis-piperidin-1-ylmethyl-cyclohexanol, 1-(4-fluoro-3-methyl-phenyl)-2,6-bis-piperidin-1-ylmethyl-cyclohexanol, 2,6-bis-piperidin-1-ylmethyl-1-o-tolyl-cyclohexanol, 2,6-bis-piperidin-1-ylmethyl-1-vinyl-cyclohexanol, 1-(4-tert-butyl-phenyl)-2,6-bis-piperidin-1-ylmethyl-cyclohexanol, 1-cyclopentyl-2,6-bis-piperidin-1-ylmethyl-cyclohexanol, 2,6-bis-piperidin-1-ylmethyl-1-m-tolyl-cyclohexanol, 2,6-bis-piperidin-1-ylmethyl-bicyclohexyl-1-ol, 1-(4-fluorophenyl)-2,6-bis-piperidin-1-ylmethyl-cyclohexanol, 1-phenethyl-2,6-bis-piperidin-1-ylmethyl-cyclohexanol, 1-phenylethynyl-2,6-bis-piperidin-1-ylmethyl-cyclohexanol, 2,6-bis-piperidin-1-ylmethyl-1-thiophen-2-yl-cyclohexanol, 1-(2,4-dichlorophenyl)-2,6-bis-piperidin-1-ylmethyl-cyclohexanol, 1-(3-methoxy-phenyl)-2,6-bis-piperidin-1-ylmethyl-cyclohexanol, 1-(3-phenyl-propyl)-2,6-bis-piperidin-1-ylmethyl-cyclohexanol, 1-(2,3-dichlorophenyl)-2,6-bis-piperidin-1-ylmethyl-cyclohexanol, 2,6-bis-piperidin-1-ylmethyl-1-p-tolyl-cyclohexanol, 1-(4-methoxy-phenyl)-2,6-bis-piperidin-1-ylmethyl-cyclohexanol, 1-cyclohexylmethyl-2,6-bis-piperidin-1-ylmethyl-cyclohexanol, 1-(5-fluoro-2-methoxy-phenyl)-2,6-bis-piperidin-1-ylmethyl-cyclohexanol, 1-(3-fluorophenyl)-2,6-bis-piperidin-1-ylmethyl-cyclohexanol, 1-(3-chlorophenyl)-2,6-bis-piperidin-1-ylmethyl-cyclohexanol, 1-(3,5-dichlorophenyl)-2,6-bis-piperidin-1-ylmethyl-cyclohexanol, 1-(2-chlorobenzyl)-2,6-bis-piperidin-1-ylmethyl-cyclohexanol, 1-(4-fluorobenzyl)-2,6-bis-piperidin-1-ylmethyl-cyclohexanol, 1-(3-methoxy-benzyl)-2,6-bis-piperidin-1-ylmethyl-cyclohexanol, 1-(4-chloro-3-trifluoromethyl-phenyl)-2,6-bis-piperidin-1-ylmethyl-cyclohexanol, 1-(3-fluorobenzyl)-2,6-bis-piperidin-1-ylmethyl-cyclohexanol, 1-(2-methoxy-phenyl)-2,6-bis-piperidin-1-ylmethyl-cyclohexanol, 1-(2-methyl-benzyl)-2,6-bis-piperidin-1-ylmethyl-cyclohexanol, 1-(3-chloro-4-fluorophenyl)-2,6-bis-piperidin-1-ylmethyl-cyclohexanol, 2,6-bis-piperidin-1-ylmethyl-1-(3-trifluoromethyl-phenyl)-cyclohexanol, 1-(3-methyl-benzyl)-2,6-bis-piperidin-1-ylmethyl-cyclohexanol, 1-(4-chlorobenzyl)-2,6-bis-piperidin-1-ylmethyl-cyclohexanol, 1-(2-chloro-6-fluorobenzyl)-2,6-bis-piperidin-1-ylmethyl-cyclohexanol, 1-(2,5-dimethyl-benzyl)-2,6-bis-piperidin-1-ylmethyl-cyclohexanol, 1-(3-chlorobenzyl)-2,6-bis-piperidin-1-ylmethyl-cyclohexanol and 1-(2,4-dichlorobenzyl)-2,6-bis-piperidin-1-ylmethyl-cyclohexanol, in the form of their racemates, their pure stereoisomers, in particular enantiomers or diastereomers, or in the form of mixtures of the stereoisomers, in particular the enantiomers or diastereomers, in any mixing ratio or each in the form of their bases or in the form of their salts, in particular the physiologically acceptable salt, or in the form of their solvates, in particular the hydrates.

The present invention also relates to methods for producing substituted 1,5-diaminopentan-3-ol compounds corresponding to formula I, wherein $A_1$) a ketone corresponding to formula (1), wherein $R^1$ and $R^2$ have the meaning given above

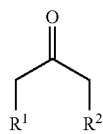
(1)

is gradually reacted with paraformaldehyde and a respective amine corresponding to formula (2) or (2a), wherein $R^4$, $R^5$, $R^6$ and $R^7$ have the meaning given above and wherein the amines corresponding to formulae (2) and (2a) are preferably the same,

(2)

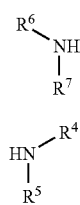
(2a)

by a Mannich reaction in a suitable solvent, preferably in ethanol, with the addition of hydrochloric acid or in acetic acid while heating, then the reaction mixture is worked up, the product corresponding to formula (3) isolated and optionally purified, or

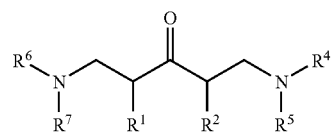
(3)

$A_2$) an enamine corresponding to formula (1a), wherein $R^1$ and $R^2$ have the meaning given above and R represents an aliphatic $C_{1-6}$ radical, a morpholinyl, piperidyl or pyrrolidinyl radical, wherein the two radicals R may be the same or different

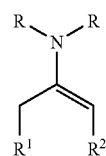
(1a)

is reacted with an aldehyde corresponding to formula (4), wherein $R^8$ has the meaning given above with the exception of hydrogen

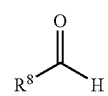
(4)

and an amine corresponding to formula (2a), wherein $R^4$ and $R^5$ have the meaning given above, optionally in the form of its hydrochloride (2a)

by a Mannich reaction in the presence of triethylamine, chlorotrimethylsilane and sodium iodide in a suitable solvent, preferably in acetonitrile, then the reaction mixture is worked up, the ketone corresponding to formula (3a) isolated and optionally purified, and (3a)

then the ketone corresponding to formula (3a) is reacted with paraformaldehyde and an amine corresponding to formula (2), wherein $R^6$ and $R^7$ have the meaning given above and wherein the amine corresponding to formula (2) is preferably the same as the amine corresponding to formula (2a)

(2)

by a Mannich reaction in a suitable solvent, preferably in ethanol, with the addition of hydrochloric acid or in acetic acid while heating, then the reaction mixture is worked up, the product corresponding to formula (3b) isolated and optionally purified, or

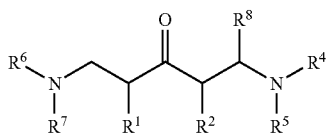
(3b)

A$_3$) an enamine corresponding to formula (1a), wherein R$^1$ and R$^2$ have the meaning given above and R represents an aliphatic C$_{1-6}$ radical, a morpholinyl, piperidyl or pyrrolidinyl radical, wherein the two radicals R may be the same or different

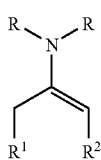
(1a)

is reacted while heating with an iminium salt corresponding to formula (5), wherein R$^8$ has the meaning given above with the exception of hydrogen and R$^4$ and R$^5$ have the meaning given above and Y$^-$ represents a chloride, bromide, iodide or AlCl$_4^-$ ion

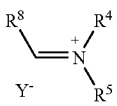
(5)

by a Mannich reaction in a suitable solvent, preferably in acetonitrile, then the reaction mixture is worked up, the ketone corresponding to formula (3a) isolated and optionally purified, and

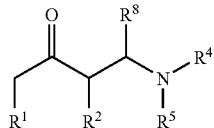
(3a)

then the ketone corresponding to formula (3a) is reacted with paraformaldehyde and an amine corresponding to formula (2), wherein R$^6$ and R$^7$ have the meaning given above and wherein the amine corresponding to formula (2) is preferably the same as the amine corresponding to formula (2a)

(2)

by a Mannich reaction in a suitable solvent, preferably in ethanol, with the addition of hydrochloric acid or in acetic acid while heating, then the reaction mixture is worked up, the product corresponding to formula (3b) isolated and optionally purified, and

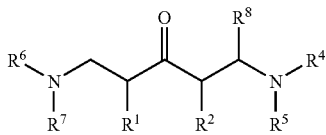
(3b)

B) a compound corresponding to formula (3) or (3b) is reacted with a Grignard compound or an organolithium compound of formulae R$^3$MgCl, R$^3$MgBr, R$^3$MgI, MgR$^3{}_2$ or LiR$^3$, wherein R$^3$ has the meaning given above, in a suitable solvent, preferably diethylether or tetrahydrofuran, then the reaction mixture is worked up, the compound corresponding to formula 1 isolated and optionally purified.

The starting compounds used are commercially available or may be obtained by methods known to a person skilled in the art.

The solvents and reaction conditions used for the respective stage of the method correspond to the solvents and reaction conditions conventional for these types of reactions. Further, the general reactions are known to a person skilled in the art from the literature.

The free bases of the respective compounds according to the invention corresponding to formula I and corresponding stereoisomers may be converted into the corresponding physiologically acceptable salts by reaction with an inorganic or organic acid, preferably with hydrochloric acid, hydrobromic acid, sulphuric acid, phosphoric acid, methane sulphonic acid, toluene-p-sulphonic acid, carbonic acid, formic acid, acetic acid, oxalic acid, succinic acid, tartaric acid, mandelic acid, fumaric acid, lactic acid, citric acid, glutamic acid or aspartic acid. The salts formed are inter alia hydrochlorides, hydrobromides, phosphates, carbonates, hydrogen carbonates, formates, acetates, oxalates, succinates, tartrates, fumarates, citrates and glutaminates.

The free bases of the respective compounds according to the invention corresponding to formula I and corresponding stereoisomers may be converted into the corresponding hydrochlorides by adding trimethylsilylchloride (TMSCl) to the compounds according to the invention corresponding to formula I dissolved in a suitable organic solvent, such as butan-2-one (methyl ethyl ketone), or corresponding stereoisomers as free bases. They may also be converted into the hydrobromides in a corresponding manner.

The free bases of the respective compounds according to the invention corresponding to formula I and corresponding stereoisomers may be converted into the corresponding physiologically acceptable salts with the free acid or a salt of a sugar substitute, such as saccharine, cyclamate or acesulphame.

The hydrates may be formed by crystallization from aqueous solution.

If the compounds according to the invention corresponding to formula I are obtained by the production method according to the invention in the form of their racemates or other mixtures of their various enantiomers and/or diastereomers, these may be separated and optionally isolated using conventional methods known to the person skilled in the art. Chromatographic separation, in particular liquid chromatography under normal pressure or under elevated pressure, preferably MPLC and HPLC and fractional crystallization are mentioned by way of example. In particular, individual enantiomers, for example diastereomic salts formed by means of HPLC on the chiral phase or by means of crystallization with chiral acids, for example (+)-tartaric acid, (−)-tartaric acid or (+)-10-camphorsulphonic acid, may be separated from one another.

The compounds according to the invention corresponding to formula I and corresponding stereoisomers and the respective corresponding bases, salts and solvates are toxicologically safe and are therefore suitable as pharmaceutical active ingredients in pharmaceutical compositions.

The present invention therefore also relates to pharmaceutical compositions containing at least one compound according to the invention corresponding to formula I, preferably corresponding to formula II, including the compounds excepted above, in the form of their racemates, their pure stereoisomers, in particular enantiomers or diastereomers, or in the form of mixtures of the stereoisomers, in particular the enantiomers or diastereomers in any mixing ratio, or each in the form of their base or in the form of their salt, in particular a physiologically acceptable salt, or in the form of their solvate, in particular the hydrate and optionally physiologically acceptable auxiliaries.

If the compounds according to the invention corresponding to formula I or their corresponding physiologically acceptable bases, salts or solvates are chiral, they may, as already stated, be present in the form of their pure enantiomers, their pure diastereomers or in the form of a mixture of at least two of the above-mentioned stereoisomers, including their racemates, in the pharmaceutical compositions according to the invention.

Preferably the pharmaceutical compositions according to the invention are suitable for controlling pain, in particular chronic and/or non-chronic pain, as a local anaesthetic, an anti-arrhythmic, anti-emetic and/or nootropic (neurotropic), for the treatment of inflammatory and/or allergic reactions, cardiovascular diseases, urinary incontinence, diarrhea, gastritis, ulcers, shock, migraine, narcolepsy, obesity, asthma, glaucoma, tinnitus, hyperkinetic syndrome, pruritus, alcohol and/or drug and/or medicine abuse and/or dependency and/or inflammation and/or depression and/or to increase alertness, to increase libido and/or for the treatment of neurodegenerative diseases, in particular Parkinson's disease and/or Huntington's chorea, for the treatment and/or prophylaxis of epilepsy, schizophrenia, Alzheimer's disease, stroke, cerebral ischemia, cerebral infarct and/or cerebral oedema and/or for anxiolysis and/or anaesthesia.

The invention also relates to the use of at least one compound corresponding to formula I, preferably corresponding to formula II, including the above-excepted compounds, in the form of their racemate, their pure stereoisomers, in particular enantiomers or diastereomers, or in the form of mixtures of the stereoisomers, in particular the enantiomers or diastereomers, in any mixing ratio or each in the form of their bases or in the form of their salt, in particular a physiologically acceptable salt, or in the form of their solvate, in particular the hydrate, for producing a pharmaceutical composition for controlling pain, in particular chronic and/or non-chronic pain, for a local anaesthetic, for the treatment of arrhythmia, emesis, inflammatory and/or allergic reactions, cardiovascular diseases, urinary incontinence, diarrhea, gastritis, ulcers, shock, migraine, narcolepsy, obesity, asthma, glaucoma, tinnitus, hyperkinetic syndrome, pruritus, alcohol and/or drug and/or medicine abuse and/or dependency and/or inflammation, depression and/or to increase drive, alertness and/or libido and/or for the treatment of neurodegenerative diseases, in particular Parkinson's disease and/or Huntington's chorea, for the treatment and/or prophylaxis of epilepsy, schizophrenia, Alzheimer's disease, stroke, cerebral ischemia, cerebral infarct and/or cerebral oedema and/or for anxiolysis and/or anaesthesia.

The pharmaceutical compositions according to the invention can be formulated as liquid, semi-solid or solid pharmaceutical forms, for example in the form of injection solutions, drops, liquids, syrups, sprays, suspensions, tablets, patches, capsules, plasters, suppositories, ointments, creams, lotions, gels, emulsions, aerosols or in multi-particulate form, for example in the form of pellets or granules and also administered as such.

In addition to at least one compound according to the invention corresponding to formula I, preferably corresponding to formula II, including the above-excepted compounds, in the form of their racemate, their pure stereoisomers, in particular enantiomers or diastereomers, or in the form of mixtures of the stereoisomers, in particular of the enantiomers or diastereomers, in any mixing ratio or each in the form of their base or in the form of their salt, in particular a physiologically acceptable salt, or in the form of their solvate, in particular the hydrate, the pharmaceutical compositions according to the invention conventionally contain further physiologically acceptable pharmaceutical auxiliaries which are preferably selected from the group comprising excipients, fillers, solvents, diluents, surface-active substances, dyes, preservatives, blasting agents, lubricants, flavors and binders.

The choice of physiologically acceptable auxiliaries and the amounts thereof to be used depend on whether the pharmaceutical composition is to be applied orally, subcutaneously, parenterally, intravenously, intraperitoneally, intradermally, intramuscularly, intranasally, buccally, rectally or topically, for example to infections of the skin, the mucous membranes and the eyes. Preparations in the form of tablets, dragees, capsules, granules, pellets, drops, liquids and syrups are suitable for oral application; solutions, suspensions, easily reconstitutable dry preparations and sprays are suitable for parenteral, topical and inhalative application. Compounds according to the invention corresponding to formula I, preferably corresponding to formula II, including the above-excepted compounds, in the form of their racemates, their pure stereoisomers, in particular enantiomers or diastereomers, or in the form of mixtures of the stereoisomers, in particular of the enantiomers or diastereomers, in any mixing ratio or each in the form of their base or in the form of their salt, in particular a physiologically acceptable salt, or in the form of their solvate, in particular the hydrate in a deposit in dissolved form or in a plaster, optionally with the addition of substances promoting skin penetration, are preparations suitable for percutaneous application.

Pharmaceutical compositions according to the invention are produced using conventional substances, devices, methods and processes known to a person skilled in the art, as are described, for example, in A. R. Gennaro (Editor), Remington's Pharmaceutical Sciences, 17th edition, Mack Publishing Company, Easton, Pa. (1985) in particular in part 8, chapter 76 to 93. The corresponding description of the literature is hereby incorporated by a reference and forms part of the disclosure.

The amount of the respective compound according to the invention corresponding to formula I, preferably corresponding to formula II, including the above-excepted compounds, in the form of their racemates, their pure stereoisomers, in particular enantiomers or diastereomers, or in the form of mixtures of the stereoisomers, in particular of the enantiomers or diastereomers, in any mixing ratio or each in the form of their base or in the form of their salt, in particular a physiologically acceptable salt, or in the form of their solvate, in particular the hydrate, to be administered to the patient, may vary and is dependent, for example, on the patient's weight or age and on the method of application, the indication and the severity of the disease. It is normal to administer 0.005 to 500 mg/kg, preferably 0.05 to 5 mg/kg body weight of the patient of at least one compound corresponding to formula I, preferably corresponding to formula II, including the above-excepted compounds, in the form of their racemate, their pure stereoisomers, in particular enantiomers or diastereomers, or in the form of mixtures of the stereoisomers, in particular of the enantiomers or diastereomers, in any mixing ratio or each in the form of their base or in the form of their salt, in particular a physiologically acceptable salt, or in the form of their solvate, in particular the hydrate.

Method for Determining the Binding Affinity to Human Alpha2A-adrenergic Receptor The affinity of the compounds according to the invention to the pain-relevant alpha2A-receptor was investigated as follows.

The receptor affinity of the compounds according to the invention to human alpha2A-adrenergic receptor was determined in a microtiter plate batch. For this purpose, the compounds to be tested were incubated in a concentration of 10 μmol/l with a receptor membrane preparation of human HT29 cells (RB-HAL2A, NEN, Zaventem, Belgium), which endogenously express the alpha2A-adrenergic receptor, at a protein concentration of 40 μg protein/250 μl incubation batch in the presence of 0.5 nmol/l of the radioactively marked ligands [3H]-MK-912 (NET-1059, NEN, Zaventem, Belgium) for 30 minutes, with exclusion of light, at ambient temperature. A 25 mmol/l sodium phosphate buffer at a pH of 7.4 was used as the buffer system. The unspecific bond was determined in the presence of 10 μmol/l phentolamine. After incubation, the microtiter plates were filtered on glass fiber microtiter filter plates (Whatman GF/B, Hassel, Munich) using a Brandel Cell Harvester (MPRI-96T type, Hassel, Munich) and after drying of the glass fiber filter plates and subsequent charging of the plates with 35 μl of a scintillator (Ultima Gold, Canberra-Packard, Freiburg) were measured in a microtiter plate counter (1450 Microbeta Trilux, PerkinElmer-Wallac, Freiburg) after a delay of at least 90 minutes. The glass fiber microtiter filter plates were each pretreated prior to filtration of the incubation plates for 30 minutes with 50 μl per indentation of a 25 mmol/l sodium phosphate buffer supplemented by 0.5% (v/v) polyethylene imine at a pH of 7.4. The percentage inhibition effect of the compounds was calculated as a displacement of the radioactive ligand from its specific bond to the human alpha2A-adrenergic receptor.

The invention will be described hereinafter with reference to examples. These descriptions are merely exemplary and do not limit the general scope of the invention.

EXAMPLES

The following examples show the preparation of certain compounds in accordance with certain embodiments of the invention and related efficacy tests.

The chemicals and solvents used were obtained commercially from conventional suppliers (Acros, Avocado, Aldrich, Fluka, Lancaster, Maybridge, Merck, Sigma, TCI, etc.) or synthesized.

General Synthesis Instructions for Producing 1,5-diamino-pentan-3-ol Compounds According to Certain Embodiments of the Invention:

Mannich Reaction I 0.1 mol of the respective amino compound corresponding to formula (2a), 0.1 mol paraformaldehyde and 0.05 mol of the respective keto compound corresponding to formula (1) together with 20 ml ethanol and 0.15 ml concentrated hydrochloric acid were heated under reflux for 6 hours. 0.05 mol paraformaldehyde and 0.05 mol of the respective amino compound corresponding to formula (2) were then added, the amino compound corresponding to formula (2) preferably being identical to the respective amino compound corresponding to formula (2a), and heated under reflux for a further 10 hours. The total reaction time was 16 hours. The solvent was then distilled under vacuum, 50 ml acetone added to the residue and the mixture left to stand for several days at +7° C. to crystallize the Mannich compound corresponding to formula (3).

Mannich Reaction II

The respective amino compound corresponding to formula (2a) (1 equivalent) was added with ice cooling to a sodium iodide solution in acetonitrile (2.2 equivalents). Triethylamine (1 equivalent) and chlorotrimethylsilane (2.2 equivalents) were added dropwise. The suspension was stirred for one hour at ambient temperature. The respective aldehyde corresponding to formula (4) (1 equivalent) was added with ice cooling and the mixture stirred for one hour at ambient temperature. One equivalent of the respective enamine was added with ice cooling and the mixture stirred for two hours at ambient temperature.

Dilute hydrochloric acid was added to the batch with ice cooling and the mixture stirred for 15 minutes. The solution was washed three times with ether. A basic pH was adjusted with dilute ammonia solution and the mixture extracted with ether. After drying over magnesium sulphate the ether phase containing the desired product was evaporated. The reaction product corresponding to formula (3a) was then further reacted.

0.1 mol (1 equivalent) of the amino compound corresponding to formula (2), wherein the amino compound corresponding to formula (2) is preferably identical to the amino compound corresponding to formula (2a), 0.1 mol paraformaldehyde and 0.05 mol (0.5 equivalents) of the reaction product were heated under reflux together with 20 ml ethanol and 0.15 ml concentrated hydrochloric acid for 6 hours. The solvent was then distilled under vacuum, 50 ml acetone added to the residue and the mixture left to stand for several days at +7° C. to crystallize the Mannich compound corresponding to formula (3b).

Grignard Reaction

The Mannich compound, dissolved in THF, corresponding to formula (3) or (3b) (400 μl, 0.5 M) was introduced into a heated reaction vessel cooled under inert gas to −10° C. Two equivalents of the prepared Grignard or organolithium reagent in THF or diethylether (800 μl 0.5 M) were added while stirring. The reaction mixture was stirred at ambient temperature. After three hours the mixture was cooled again to −10° C. and hydrolyzed with ammonium chloride solution.

The reaction mixture was extracted twice with ethyl acetate and evaporated under vacuum at 40° C.

To characterize the compound according to the invention corresponding to formula I, preferably corresponding to formula II, an ESI-MS was taken in each case.

Determining the Binding Affinity to Human Alpha2A-adrenergic Receptor

The binding affinities to human alpha2A-adrenergic receptor were determined by the foregoing methods.

The values of some selected exemplary compounds are recited in the following Table 1:

TABLE 1

| Alpha2A, 10 NM [%] inhibition | Compound according to the invention |
|---|---|
| 48 | 1-(3-fluorophenyl)-2,6-bis-piperidin-1-ylmethyI-cyclohexanol |
| 51 | 1-(3-chlorophenyl)-2,6-bis-piperidin-1-ylmethyI-cyclohexanol |
| 33 | 1-(3,5-dichlorophenyl)-2,6-bis-piperidin-1-ylmethyI-cyclohexanol |
| 100 | 1-(2-chlorobenzyl)-2,6-bis-piperidin-1-ylmethyI-cyclohexanol |
| 87 | 1-(4-fluorobenzyl)-2,6-bis-piperidin-1-ylmethyI-cyclohexanol |
| 80 | 1-(3-methoxy-benzyl)-2,6-bis-piperidin-1-ylmethyI-cyclohexanol |
| 26 | 1-(4-chloro-3-trifluoromethyl-phenyl)-2,6-bis-piperidin-1-ylmethyl-cyclohexanol c cyclohexanol |
| 59 | 1-(3-fluorobenzyl)-2,6-bis-piperidin-1-ylmethyI-cyclohexanol |
| 30 | 1-(2-methoxy-phenyl)-2,6-bis-piperidin-1-ylmethyI-cyclohexanol |
| 100 | 1-(2-methyl-benzyl)-2,6-bis-piperidin-1-ylmethyI-cyclohexanol |
| 38 | 1-(3-chloro-4-fluoro-phenyl)-2,6-bis-piperidin-1-ylmethyl cyclohexanol |
| 56 | 2,6-bis-piperidin-1-ylmethyl-1-(3-trifluoromethyl-phenyl) cyclohexanol |
| 100 | 1-(3-methyl-benzyl)-2,6-bis-piperidin-1-ylmethyI-cyclohexanol |
| 88 | 1-(4-chlorobenzyl)-2,6-bis-piperidin-1-ylmethyI-cyclohexanol |
| 68 | 1-(2-chloro-6-fluoro-benzyl)-2,6-bis-piperidin-1-ylmethyl cyclohexanol |
| 100 | 1-(2,5-dimethyI-benzyl)-2,6-bis-piperidin-1-ylmethyI-cyclohexanol |
| 98 | 1-(3-chlorobenzyl-2,6-bis-piperidin-1-ylmethyI-cyclohexanol |
| 100 | 1-(2,4-dichlorobenzyl)-2,6-bis-piperidin-1-ylmethyI-cyclohexanol |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

The invention claimed is:

1. A 1,5-diaminopentan-3-ol compound corresponding to formula I,

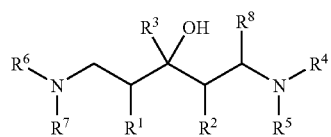

wherein
$R^1$ and $R^2$ together form a $(CH_2)_n$ chain, wherein n represents 3;
$R^3$ represents a linear or branched, saturated or unsaturated aliphatic radical, a saturated or unsaturated cycloaliphatic radical, an aryl radical or a heteroaryl radical, wherein the respective ring system is optionally singly or multiply substituted or is bound by a linear or branched, saturated or unsaturated aliphatic bridge or the aryl or heteroaryl radical is part of a polycyclic system;
$R^4$ and $R^5$ together form a $(CH_2)_m$ chain wherein m represents 5;
$R^6$ and $R^7$ together form a $(CH_2)_p$ chain, wherein p represents 5;
$R^8$ represents hydrogen or an optionally singly or multiply substituted aryl or heteroaryl radical, wherein the aryl or heteroaryl radical is optionally part of a polycyclic system;
or a physiologically acceptable salt thereof.

2. The compound of claim 1, wherein said compound is present in the form of a free base.

3. The compound of claim 1, wherein said compound is present in the form of an isolated enantiomer or isolated diastereoisomer.

4. The compound of claim 1, wherein said compound is present in the form of a mixture of stereoisomers.

5. The compound of claim 1, wherein said compound is present in the form of a racemic mixture.

6. The compound of claim 1, wherein
$R^3$ represents a linear or branched, saturated or unsaturated aliphatic $C_{1-6}$ radical, a saturated or unsaturated cycloaliphatic $C_{3-7}$ radical, a phenyl radical wherein the respective ring system is optionally singly or multiply substituted or bound by a linear or branched, saturated or unsaturated aliphatic $C_{1-5}$ bridge;
$R^8$ represents hydrogen.

7. The compound of claim 1, wherein
$R^3$ represents a linear or branched, saturated or unsaturated aliphatic $C_{1-3}$ radical, a saturated or unsaturated cycloaliphatic $C_{5-6}$ radical, a phenyl radical wherein the respective ring system is optionally singly or multiply substituted by halogen, an alkyl group, an alkoxy group or a trihalogenated alkyl group or is bound by a linear or branched, saturated or unsaturated aliphatic $C_{1-3}$ bridge; and
$R^8$ represents hydrogen.

8. The compound of claim 7, wherein the respective ring system of the radical $R^3$ is singly or multiply substituted by halogen, an alkyl group with 1 to 6 carbon atoms, an alkoxy group with 1 to 6 carbon atoms or a trihalogenated methyl group or is bound by a linear or branched, saturated or unsaturated aliphatic $C_{1-3}$ bridge.

9. The compound of claim 1, wherein
$R^3$ represents a vinyl radical, a cyclopentyl radical, a cyclohexyl radical, a thiophenyl radical or a phenyl radical, wherein the cyclohexyl radical is optionally bound by a methylene bridge or the phenyl radical is optionally singly or multiply substituted by fluorine, chlorine, a methyl group, an isopropyl group, a methoxy group or a trifluoromethyl group or is optionally bound by a linear, saturated aliphatic $C_{1-3}$ bridge or an ethinyl bridge;
$R^8$ represents hydrogen.

10. A substituted 1,5-diaminopentan-3-ol compound according to claim 1 wherein said compound is selected from the group consisting of:
1-phenyl-2,6-bis-piperidin-1-ylmethyl-cyclohexanol;
1-(4-chlorophenyl)-2,6-bis-piperidin-1-ylmethyl-cyclohexanol;
1-benzyl-2,6-bis-piperidin-1-ylmethyl-cyclohexanol;
1-(4-fluoro-3-methyl-phenyl)-2,6-bis-piperidin-1-ylmethyl-cyclohexanol;
2,6-bis-piperidin-1-ylmethyl-1-o-tolyl-cyclohexanol;
2,6-bis-piperidin-1-ylmethyl-1-vinyl-cyclohexanol;
1-(4-tert-butyl-phenyl)-2,6-bis-piperidin-1-ylmethyl-cyclohexanol;
1-cyclopentyl-2,6-bis-piperidin-1-ylmethyl-cyclohexanol;
2,6-bis-piperidin-1-ylmethyl-1-m-tolyl-cyclohexanol;
2,6-bis-piperidin-1-ylmethyl-bicyclohexyl-1-ol;

1-(4-fluorophenyl)-2,6-bis-piperidin-1-ylmethyl-cyclohexanol;
1-phenethyl-2,6-bis-piperidin-1-ylmethyl-cyclohexanol;
1-phenylethynyl-2,6-bis-piperidin-1-ylmethyl-cyclohexanol;
1-(2,4-dichlorophenyl)-2,6-bis-piperidin-1-ylmethyl-cyclohexanol;
1-(3-methoxy-phenyl)-2,6-bis-piperidin-1-ylmethyl-cyclohexanol;
1-(3-phenyl-propyl)-2,6-bis-piperidin-1-ylmethyl-cyclohexanol;
1-(2,3-dichlorophenyl)-2,6-bis-piperidin-1-ylmethyl-cyclohexanol;
2,6-bis-piperidin-1-ylmethyl-1-p-tolyl-cyclohexanol;
1-(4-methoxy-phenyl)-2,6-bis-piperidin-1-ylmethyl-cyclohexanol;
1-cyclohexylmethyl-2,6-bis-piperidin-1-ylmethyl-cyclohexanol;
1-(5-fluoro-2-methoxy-phenyl)-2,6-bis-piperidin-1-ylmethyl-cyclohexanol;
1-(3-fluorophenyl)-2,6-bis-piperidin-1-ylmethyl-cyclohexanol;
1-(3-chlorophenyl)-2,6-bis-piperidin-1-ylmethyl-cyclohexanol;
1-(3,5-dichlorophenyl)-2,6-bis-piperidin-1-ylmethyl-cyclohexanol;
1-(2-chlorobenzyl)-2,6-bis-piperidin-1-ylmethyl-cyclohexanol;
1-(4-fluorobenzyl)-2,6-bis-piperidin-1-ylmethyl-cyclohexanol;
1-(3-methoxy-benzyl)-2,6-bis-piperidin-1-ylmethyl-cyclohexanol;
1-(4-chloro-3-trifluoromethyl-phenyl)-2,6-bis-piperidin-1-ylmethyl-cyclohexanol;
1-(3-fluorobenzyl)-2,6-bis-piperidin-1-ylmethyl-cyclohexanol;
1-(2-methoxy-phenyl)-2,6-bis-piperidin-1-ylmethyl-cyclohexanol;
1-(2-methyl-benzyl)-2,6-bis-piperidin-1-ylmethyl-cyclohexanol;
1-(3-chloro-4-fluorophenyl)-2,6-bis-piperidin-1-ylmethyl-cyclohexanol;
2,6-bis-piperidin-1-ylmethyl-1-(3-trifluoromethyl-phenyl)-cyclohexanol;
1-(3-methyl-benzyl)-2,6-bis-piperidin-1-ylmethyl-cyclohexanol;
1-(4-chlorobenzyl)-2,6-bis-piperidin-1-ylmethyl-cyclohexanol;
1-(2-chloro-6-fluorobenzyl)-2,6-bis-piperidin-1-ylmethyl-cyclohexanol;
1-(2,5-dimethyl-benzyl)-2,6-bis-piperidin-1-ylmethyl-cyclohexanol;
1-(3-chlorobenzyl)-2,6-bis-piperidin-1-ylmethyl-cyclohexanol;
1-(2,4-dichlorobenzyl)-2,6-bis-piperidin-1-ylmethyl-cyclohexanol; and pharmaceutically acceptable salts thereof.

11. A method for producing a 1,5-diaminopentan-3-ol compound according to claim 1, comprising the steps of $A_1$) reacting a ketone corresponding to formula (1),

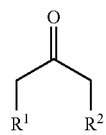
(1)

with paraformaldehyde and an amine corresponding to formula (2) or (2a),

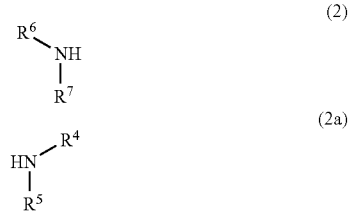
(2)

(2a)

by a Mannich reaction in a suitable solvent;
working up the reaction mixture; and
isolating the product corresponding to formula (3)

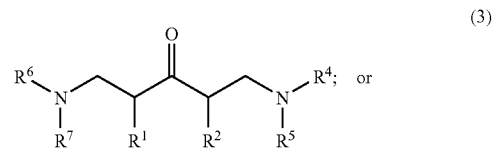
(3)

$A_2$) reacting an enamine corresponding to formula 1a wherein R represents an aliphatic $C_{1-6}$ radical, a morpholinyl, piperidyl or pyrrolidinyl radical, wherein the two radicals R are the same or different

(1a)

with an aldehyde corresponding to formula (4), wherein $R^8$ is not hydrogen

(4)

and an amine corresponding to formula (2a),

(2a)

by a Mannich reaction in the presence of triethylamine, chlorotrimethylsilane and sodium iodide in a suitable solvent;
working up the mixture; and
isolating the ketone corresponding to formula (3a);

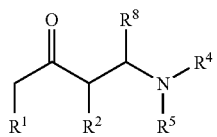

(3a)

reacting the ketone corresponding to formula (3a) with paraformaldehyde and an amine corresponding to formula (2),

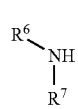

(2)

by a Mannich reaction in a suitable solvent, with the addition of hydrochloric acid or in acetic acid while heating;
working up the reaction mixture; and
isolating the product corresponding to formula (3b)

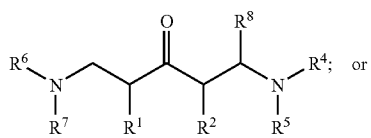

(3b)

$A_3$) reacting an enamine corresponding to formula (1a), wherein R represents an aliphatic $C_{1-6}$ radical, a morpholinyl, piperidyl or pyrrolidinyl radical, wherein the two radicals R are the same or different

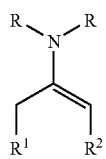

(1a)

with an iminium salt corresponding to formula (5), wherein $R^8$ is not hydrogen and Y- represents a chloride, bromide, iodide or $AlCl_4$-ion

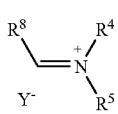

(5)

by a Mannich reaction while heating in a suitable solvent;
working up the reaction mixture;
isolating the ketone corresponding to formula (3a);

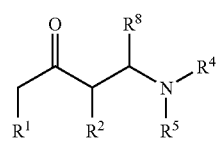

(3a)

reacting the ketone corresponding to formula (3a) with paraformaldehyde and an amine corresponding to formula (2)

(2)

by a Mannich reaction in a suitable solvent, with the addition of hydrochloric acid or in acetic acid while heating;
working up the reaction mixture;
isolating the product corresponding to formula (3b) and

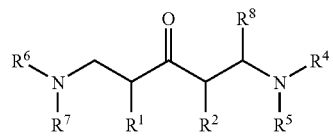

(3b)

B) reacting a compound corresponding to formula (3) or (3b) with a Grignard compound or an organolithium compound corresponding to formulae $R^3MgCl$, $R^3MgBr$, $R^3MgI$, $MgR^3{}_2$ or $LiR^3$, in a suitable solvent;
working up the reaction mixture and
isolating the compound corresponding to formula 1.

12. The method of claim 11, wherein the amines corresponding to formulae (2) and (2a) are the same.

13. The method of claim 11, wherein the solvent of step $A_1$) is ethanol, optionally with the addition of hydrochloric acid or acetic acid, wherein said reaction is optionally provided with heat.

14. The method of claim 11, wherein the amine corresponding to formula (2a) of step $A_2$) is in the form of its hydrochloride.

15. The method of claim 11, wherein the solvent of the first Mannich reaction in step $A_2$) or step $A_3$) is acetonitrile.

16. The method of claim 11, wherein the solvent of the second Mannich reaction in step $A_2$) or step $A_3$) is ethanol.

17. The method of claim 11, wherein the solvent in step B of the reaction is diethylether or tetrahydrofuran.

* * * * *

UNITED STATES PATENT AND TRADEMARK OFFICE
CERTIFICATE OF CORRECTION

PATENT NO. : 7,569,585 B2 Page 1 of 1
APPLICATION NO. : 10/866088
DATED : August 4, 2009
INVENTOR(S) : Uragg et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1212 days.

Signed and Sealed this

Seventh Day of September, 2010

David J. Kappos
*Director of the United States Patent and Trademark Office*